(12) United States Patent
Baldwin et al.

(10) Patent No.: US 7,507,772 B2
(45) Date of Patent: *Mar. 24, 2009

(54) FORMING A CHEMICALLY CROSS-LINKED PARTICLE OF A DESIRED SHAPE AND DIAMETER

(75) Inventors: Samuel P. Baldwin, Newton, MA (US); Robert P. Skribiski, Newton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/854,083

(22) Filed: Sep. 12, 2007

(65) Prior Publication Data

US 2008/0174053 A1    Jul. 24, 2008

Related U.S. Application Data

(63) Continuation of application No. 11/394,691, filed on Mar. 31, 2006, now Pat. No. 7,288,319, which is a continuation of application No. 10/402,068, filed on Mar. 28, 2003, now Pat. No. 7,053,134, which is a continuation of application No. 10/116,330, filed on Apr. 4, 2002, now abandoned.

(51) Int. Cl.
*C08J 3/28* (2006.01)
*C08J 3/24* (2006.01)
*C08F 2/46* (2006.01)

(52) U.S. Cl. .................. 522/154; 522/151; 522/88; 522/87; 522/150; 522/157; 522/162; 522/166; 522/90; 522/152; 428/402; 264/429; 264/460; 264/461; 264/463; 264/478; 264/485; 264/488; 264/494; 264/496; 526/129; 526/200

(58) Field of Classification Search ................. 522/154, 522/151, 88, 87, 150, 157, 162, 166, 90, 522/152; 428/402; 264/429, 460, 461, 463, 264/478, 485, 488, 494, 496; 526/124, 200
See application file for complete search history.

(56) References Cited

U.S. PATENT DOCUMENTS

| | | | |
|---|---|---|---|
| 2,275,154 A | 3/1942 | Merrill et al. |
| 2,609,347 A | 9/1952 | Wilson |
| 3,663,470 A | 5/1972 | Nishimura et al. |
| 3,737,398 A | 6/1973 | Yamaguchi |
| 3,957,933 A | 5/1976 | Egli et al. |
| 4,025,686 A | 5/1977 | Zion |
| 4,034,759 A | 7/1977 | Haerr |
| 4,055,377 A | 10/1977 | Erickson et al. |
| 4,076,640 A | 2/1978 | Forgensi et al. |
| 4,094,848 A | 6/1978 | Naito |
| 4,096,230 A | 6/1978 | Haerr |
| 4,098,728 A | 7/1978 | Rosenblatt |
| 4,110,529 A | 8/1978 | Stoy |
| 4,159,719 A | 7/1979 | Haerr |
| 4,191,672 A | 3/1980 | Salome et al. |
| 4,198,318 A | 4/1980 | Stowell et al. |
| 4,243,794 A | 1/1981 | White et al. |
| 4,246,208 A | 1/1981 | Dundas |
| 4,266,030 A | 5/1981 | Tschang et al. |
| 4,268,495 A | 5/1981 | Muxfeldt et al. |
| 4,271,281 A | 6/1981 | Kelley et al. |
| 4,402,319 A | 9/1983 | Handa et al. |
| 4,413,070 A | 11/1983 | Rembaum |
| 4,427,794 A | 1/1984 | Lange et al. |
| 4,428,869 A | 1/1984 | Munteanu et al. |
| 4,429,062 A | 1/1984 | Pasztor et al. |
| 4,442,843 A | 4/1984 | Rasor et al. |
| 4,444,961 A | 4/1984 | Timm |
| 4,452,773 A | 6/1984 | Molday |
| 4,456,693 A | 6/1984 | Welsh |
| 4,459,145 A | 7/1984 | Elsholz |
| 4,472,552 A | 9/1984 | Blouin |
| 4,477,255 A | 10/1984 | Pasztor et al. |
| 4,492,720 A | 1/1985 | Mosier |
| 4,522,953 A | 6/1985 | Barby et al. |
| 4,542,178 A | 9/1985 | Zimmermann et al. |
| 4,551,132 A | 11/1985 | Pasztor et al. |
| 4,551,436 A | 11/1985 | Johnson et al. |

(Continued)

FOREIGN PATENT DOCUMENTS

AU    A-76186/98    10/1998

(Continued)

OTHER PUBLICATIONS

Abbara et al., "Transcervical Expulsion of a Fibroid as a Result of Uterine Artery Embolization for Leiomyomata", JVIR, vol. 10, No. 4, pp. 409-411, 1999.

(Continued)

*Primary Examiner*—Sanza L McClendon
(74) *Attorney, Agent, or Firm*—Fish & Richardson P.C.

(57) ABSTRACT

Chemically cross-linked polymeric particles are formed using mechanical rather than chemical processes, facilitating production of small-diameter particles in a manner largely independent of the viscosity or density of the polymer. For example, an uncross-linked resin may be provided in particulate form, agglomerated, and compressed into a mass of a desired shape with a desired diameter, and subsequently cross-linked.

21 Claims, 1 Drawing Sheet

U.S. PATENT DOCUMENTS

| | | |
|---|---|---|
| 4,573,967 A | 3/1986 | Hargrove et al. |
| 4,622,362 A | 11/1986 | Rembaum |
| 4,623,706 A | 11/1986 | Timm et al. |
| 4,640,807 A | 2/1987 | Afghan et al. |
| 4,657,756 A | 4/1987 | Rasor et al. |
| 4,661,137 A | 4/1987 | Garnier et al. |
| 4,663,358 A | 5/1987 | Hyon et al. |
| 4,671,954 A | 6/1987 | Goldberg et al. |
| 4,674,480 A | 6/1987 | Lemelson |
| 4,675,113 A | 6/1987 | Graves et al. |
| 4,678,710 A | 7/1987 | Sakimoto et al. |
| 4,678,814 A | 7/1987 | Rembaum |
| 4,680,320 A | 7/1987 | Uku et al. |
| 4,681,119 A | 7/1987 | Rasor et al. |
| 4,695,466 A | 9/1987 | Morishita et al. |
| 4,713,076 A | 12/1987 | Draenert |
| 4,742,086 A | 5/1988 | Masamizu et al. |
| 4,743,507 A | 5/1988 | Franses et al. |
| 4,772,635 A | 9/1988 | Mitschker et al. |
| 4,782,097 A | 11/1988 | Jain et al. |
| 4,789,501 A | 12/1988 | Day et al. |
| 4,793,980 A | 12/1988 | Torobin |
| 4,795,741 A | 1/1989 | Leshchiner et al. |
| 4,801,458 A | 1/1989 | Hidaka et al. |
| 4,804,366 A | 2/1989 | Zdeb et al. |
| 4,819,637 A | 4/1989 | Dormandy, Jr. et al. |
| 4,822,535 A | 4/1989 | Ekman et al. |
| 4,833,237 A | 5/1989 | Kawamura et al. |
| 4,850,978 A | 7/1989 | Dudar et al. |
| 4,859,711 A | 8/1989 | Jain et al. |
| 4,863,972 A | 9/1989 | Itagaki et al. |
| 4,897,255 A | 1/1990 | Fritzberg et al. |
| 4,929,400 A | 5/1990 | Rembaum et al. |
| 4,933,372 A | 6/1990 | Feibush et al. |
| 4,946,899 A | 8/1990 | Kennedy et al. |
| 4,954,399 A | 9/1990 | Tani et al. |
| 4,981,625 A | 1/1991 | Rhim et al. |
| 4,990,340 A | 2/1991 | Hidaka et al. |
| 4,999,188 A | 3/1991 | Sloldovnik et al. |
| 5,007,940 A | 4/1991 | Berg |
| 5,011,677 A | 4/1991 | Day et al. |
| H915 H | 5/1991 | Gibbs |
| 5,015,423 A | 5/1991 | Eguchi et al. |
| 5,032,117 A | 7/1991 | Motta |
| 5,034,324 A | 7/1991 | Shinozaki et al. |
| 5,047,438 A | 9/1991 | Feibush et al. |
| 5,079,274 A | 1/1992 | Schneider et al. |
| 5,091,205 A | 2/1992 | Fan |
| 5,106,903 A | 4/1992 | Vanderhoff et al. |
| 5,114,421 A | 5/1992 | Polak |
| 5,116,387 A | 5/1992 | Berg |
| 5,120,349 A | 6/1992 | Stewart et al. |
| 5,125,892 A | 6/1992 | Drudik |
| 5,147,631 A | 9/1992 | Glajch et al. |
| 5,147,937 A | 9/1992 | Frazza et al. |
| 5,149,543 A | 9/1992 | Cohen et al. |
| 5,158,573 A | 10/1992 | Berg |
| 5,171,214 A | 12/1992 | Kolber et al. |
| 5,171,217 A | 12/1992 | March et al. |
| 5,181,921 A | 1/1993 | Makita et al. |
| 5,190,760 A | 3/1993 | Baker |
| 5,190,766 A | 3/1993 | Ishihara |
| 5,192,301 A | 3/1993 | Kamiya et al. |
| 5,202,352 A | 4/1993 | Okada et al. |
| 5,216,096 A | 6/1993 | Hattori et al. |
| 5,253,991 A | 10/1993 | Yokota et al. |
| 5,260,002 A | 11/1993 | Wang |
| 5,262,176 A | 11/1993 | Palmacci et al. |
| 5,263,992 A | 11/1993 | Guire |
| 5,288,763 A | 2/1994 | Li et al. |
| 5,292,814 A | 3/1994 | Bayer et al. |
| 5,302,369 A | 4/1994 | Day et al. |
| 5,314,974 A | 5/1994 | Ito et al. |
| 5,316,774 A | 5/1994 | Eury et al. |
| RE34,640 E | 6/1994 | Kennedy et al. |
| 5,320,639 A | 6/1994 | Rudnick |
| 5,328,936 A | 7/1994 | Leifholtz et al. |
| 5,336,263 A | 8/1994 | Ersek et al. |
| 5,344,452 A | 9/1994 | Lemperle |
| 5,344,867 A | 9/1994 | Morgan et al. |
| 5,354,290 A | 10/1994 | Gross |
| 5,369,133 A | 11/1994 | Ihm et al. |
| 5,369,163 A | 11/1994 | Chiou et al. |
| 5,382,260 A | 1/1995 | Dormandy, Jr. et al. |
| 5,384,124 A | 1/1995 | Courteille et al. |
| 5,397,303 A | 3/1995 | Sancoff et al. |
| 5,398,851 A | 3/1995 | Sancoff et al. |
| 5,403,870 A | 4/1995 | Gross |
| 5,417,982 A | 5/1995 | Modi |
| 5,431,174 A | 7/1995 | Knute |
| 5,435,645 A | 7/1995 | Faccioli et al. |
| 5,443,495 A | 8/1995 | Buscemi et al. |
| 5,456,693 A | 10/1995 | Conston et al. |
| 5,468,801 A | 11/1995 | Antonelli et al. |
| 5,469,854 A | 11/1995 | Unger et al. |
| 5,476,472 A | 12/1995 | Dormandy, Jr. et al. |
| 5,484,584 A | 1/1996 | Wallace et al. |
| 5,490,984 A | 2/1996 | Freed |
| 5,494,682 A | 2/1996 | Cohen et al. |
| 5,494,940 A | 2/1996 | Unger et al. |
| 5,512,604 A | 4/1996 | Demopolis |
| 5,514,090 A | 5/1996 | Kriesel et al. |
| 5,525,334 A | 6/1996 | Ito et al. |
| 5,534,589 A | 7/1996 | Hager et al. |
| 5,541,031 A | 7/1996 | Yamashita et al. |
| 5,542,935 A | 8/1996 | Unger et al. |
| 5,553,741 A | 9/1996 | Sancoff et al. |
| 5,556,391 A | 9/1996 | Cercone et al. |
| 5,556,610 A | 9/1996 | Yan et al. |
| 5,558,255 A | 9/1996 | Sancoff et al. |
| 5,558,822 A | 9/1996 | Gitman et al. |
| 5,558,856 A | 9/1996 | Klaveness et al. |
| 5,559,266 A | 9/1996 | Klaveness et al. |
| 5,567,415 A | 10/1996 | Porter |
| 5,569,193 A | 10/1996 | Hofstetter et al. |
| 5,569,449 A | 10/1996 | Klaveness et al. |
| 5,569,468 A | 10/1996 | Modi |
| 5,571,182 A | 11/1996 | Ersek et al. |
| 5,578,709 A | 11/1996 | Woiszwillo |
| 5,580,575 A | 12/1996 | Unger et al. |
| 5,583,162 A | 12/1996 | Li et al. |
| 5,585,112 A | 12/1996 | Unger et al. |
| 5,595,821 A | 1/1997 | Hager et al. |
| 5,622,657 A | 4/1997 | Takada et al. |
| 5,624,685 A | 4/1997 | Takahashi et al. |
| 5,635,215 A | 6/1997 | Boschetti et al. |
| 5,637,087 A | 6/1997 | O'Neil et al. |
| 5,639,710 A | 6/1997 | Lo et al. |
| 5,648,095 A | 7/1997 | Illum et al. |
| 5,648,100 A | 7/1997 | Boschetti et al. |
| 5,650,116 A | 7/1997 | Thompson |
| 5,651,990 A | 7/1997 | Takada et al. |
| 5,653,922 A | 8/1997 | Li et al. |
| 5,657,756 A | 8/1997 | Vrba |
| 5,681,576 A | 10/1997 | Henry |
| 5,695,480 A | 12/1997 | Evans et al. |
| 5,695,740 A | 12/1997 | Porter |
| 5,698,271 A | 12/1997 | Liberti et al. |
| 5,701,899 A | 12/1997 | Porter |
| 5,715,824 A | 2/1998 | Unger et al. |
| 5,716,981 A | 2/1998 | Hunter et al. |
| 5,718,884 A | 2/1998 | Klaveness et al. |
| 5,723,269 A | 3/1998 | Akagi et al. |
| 5,725,534 A | 3/1998 | Rasmussen |

| | | | | | |
|---|---|---|---|---|---|
| 5,733,925 | A | 3/1998 | Kunz et al. | 6,224,630 B1 | 5/2001 | Bao et al. |
| 5,741,331 | A | 4/1998 | Pinchuk | 6,224,794 B1 | 5/2001 | Amsden et al. |
| 5,746,734 | A | 5/1998 | Dormandy, Jr. et al. | 6,235,224 B1 | 5/2001 | Mathiowitz et al. |
| 5,752,974 | A | 5/1998 | Rhee et al. | 6,238,403 B1 | 5/2001 | Greene, Jr. et al. |
| 5,756,127 | A | 5/1998 | Grisoni et al. | 6,245,090 B1 | 6/2001 | Gilson et al. |
| 5,760,097 | A | 6/1998 | Li et al. | 6,251,661 B1 | 6/2001 | Urabe et al. |
| 5,766,147 | A | 6/1998 | Sancoff et al. | 6,258,338 B1 | 7/2001 | Gray |
| 5,770,222 | A | 6/1998 | Unger et al. | 6,261,585 B1 | 7/2001 | Sefton et al. |
| 5,779,668 | A | 7/1998 | Grabenkort | 6,264,861 B1 | 7/2001 | Tavernier et al. |
| 5,785,642 | A | 7/1998 | Wallace et al. | 6,267,154 B1 | 7/2001 | Felicelli et al. |
| 5,785,682 | A | 7/1998 | Grabenkort | 6,268,053 B1 | 7/2001 | Woiszwillo et al. |
| 5,792,478 | A | 8/1998 | Lawin et al. | 6,277,392 B1 | 8/2001 | Klein |
| 5,795,562 | A | 8/1998 | Klaveness et al. | 6,280,457 B1 | 8/2001 | Wallace et al. |
| 5,797,953 | A | 8/1998 | Tekulve | 6,291,605 B1 | 9/2001 | Freeman et al. |
| 5,807,323 | A | 9/1998 | Kriesel et al. | 6,296,604 B1 | 10/2001 | Garibaldi et al. |
| 5,813,411 | A | 9/1998 | Van Bladel et al. | 6,296,622 B1 | 10/2001 | Kurz et al. |
| 5,823,198 | A | 10/1998 | Jones et al. | 6,296,632 B1 | 10/2001 | Luscher et al. |
| 5,827,502 | A | 10/1998 | Klaveness et al. | 6,306,418 B1 | 10/2001 | Bley |
| 5,827,531 | A | 10/1998 | Morrison et al. | 6,306,419 B1 | 10/2001 | Vachon et al. |
| 5,830,178 | A | 11/1998 | Jones et al. | 6,306,425 B1 | 10/2001 | Tice et al. |
| 5,833,361 | A | 11/1998 | Funk | 6,306,427 B1 | 10/2001 | Annonier et al. |
| 5,840,387 | A | 11/1998 | Berlowitz-Tarrant et al. | 6,312,407 B1 | 11/2001 | Zadno-Azizi et al. |
| 5,846,518 | A | 12/1998 | Yan et al. | 6,312,942 B1 | 11/2001 | Plüss-Wenzinger et al. |
| 5,853,752 | A | 12/1998 | Unger et al. | 6,315,709 B1 | 11/2001 | Garibaldi et al. |
| 5,855,615 | A | 1/1999 | Bley et al. | 6,335,384 B1 | 1/2002 | Evans et al. |
| 5,863,957 | A | 1/1999 | Li et al. | 6,344,182 B1 | 2/2002 | Sutton et al. |
| 5,876,372 | A | 3/1999 | Grabenkort et al. | 6,355,275 B1 | 3/2002 | Klein |
| 5,877,224 | A | 3/1999 | Brocchini et al. | 6,368,658 B1 | 4/2002 | Schwarz et al. |
| 5,885,216 | A | 3/1999 | Evans, III et al. | 6,379,373 B1 | 4/2002 | Sawhney et al. |
| 5,885,547 | A | 3/1999 | Gray | 6,388,043 B1 | 5/2002 | Langer et al. |
| 5,888,546 | A | 3/1999 | Ji et al. | 6,394,965 B1 | 5/2002 | Klein |
| 5,888,930 | A | 3/1999 | Smith et al. | 6,423,332 B1 | 7/2002 | Huxel et al. |
| 5,891,155 | A | 4/1999 | Irie | 6,432,437 B1 | 8/2002 | Hubbard |
| 5,894,022 | A | 4/1999 | Ji et al. | 6,436,112 B2 | 8/2002 | Wensel et al. |
| 5,895,398 | A | 4/1999 | Wensel et al. | 6,443,941 B1 | 9/2002 | Slepian et al. |
| 5,895,411 | A | 4/1999 | Irie | 6,458,296 B1 | 10/2002 | Heinzen et al. |
| 5,899,877 | A | 5/1999 | Leibitzki et al. | 6,476,069 B2 | 11/2002 | Krall et al. |
| 5,902,832 | A | 5/1999 | Van Bladel et al. | 6,495,155 B1 | 12/2002 | Tice et al. |
| 5,902,834 | A | 5/1999 | Porrvik | 6,544,503 B1 | 4/2003 | Vanderhoff et al. |
| 5,922,025 | A | 7/1999 | Hubbard | 6,544,544 B2 | 4/2003 | Hunter et al. |
| 5,922,304 | A | 7/1999 | Unger | 6,545,097 B2 | 4/2003 | Pinchuk et al. |
| 5,928,626 | A | 7/1999 | Klaveness et al. | 6,575,896 B2 | 6/2003 | Silverman et al. |
| 5,935,553 | A | 8/1999 | Unger et al. | 6,602,261 B2 | 8/2003 | Greene, Jr. et al. |
| 5,951,160 | A | 9/1999 | Ronk | 6,602,524 B2 | 8/2003 | Batich et al. |
| 5,957,848 | A | 9/1999 | Sutton et al. | 6,605,111 B2 | 8/2003 | Bose et al. |
| 5,959,073 | A | 9/1999 | Schlameus et al. | 6,629,947 B1 | 10/2003 | Sahatjian et al. |
| 6,003,566 | A | 12/1999 | Thibault et al. | 6,632,531 B2 | 10/2003 | Blankenship |
| 6,015,546 | A | 1/2000 | Sutton et al. | 6,652,883 B2 | 11/2003 | Goupil et al. |
| 6,027,472 | A | 2/2000 | Kriesel et al. | 6,680,046 B1 | 1/2004 | Boschetti |
| 6,028,066 | A | 2/2000 | Unger | 6,699,222 B1 | 3/2004 | Jones et al. |
| 6,047,861 | A | 4/2000 | Vidal et al. | 7,053,134 B2 | 5/2006 | Baldwin et al. |
| 6,048,908 | A | 4/2000 | Kitagawa | 7,131,997 B2 | 11/2006 | Bourne et al. |
| 6,051,247 | A | 4/2000 | Hench et al. | 2001/0001835 A1 | 5/2001 | Greene, Jr. et al. |
| 6,056,721 | A | 5/2000 | Shulze | 2001/0016210 A1 | 8/2001 | Mathiowitz et al. |
| 6,056,844 | A | 5/2000 | Guiles et al. | 2001/0036451 A1 | 11/2001 | Goupil et al. |
| 6,059,766 | A | 5/2000 | Greff | 2001/0051670 A1 | 12/2001 | Goupil et al. |
| 6,063,068 | A | 5/2000 | Fowles et al. | 2002/0054912 A1 | 5/2002 | Kim et al. |
| 6,071,495 | A | 6/2000 | Unger et al. | 2002/0061954 A1 | 5/2002 | Davis et al. |
| 6,071,497 | A | 6/2000 | Steiner et al. | 2002/0160109 A1 | 10/2002 | Yeo et al. |
| 6,073,759 | A | 6/2000 | Lamborne et al. | 2002/0182190 A1 | 12/2002 | Naimark et al. |
| 6,090,925 | A | 7/2000 | Woiszwillo et al. | 2002/0197208 A1 | 12/2002 | Ruys et al. |
| 6,096,344 | A | 8/2000 | Liu et al. | 2003/0007928 A1 | 1/2003 | Gray |
| 6,099,864 | A | 8/2000 | Morrison et al. | 2003/0032935 A1 | 2/2003 | Damiano et al. |
| 6,100,306 | A | 8/2000 | Li et al. | 2003/0108614 A1 | 6/2003 | Volkonsky et al. |
| 6,139,963 | A | 10/2000 | Fujii et al. | 2003/0183962 A1 | 10/2003 | Buiser et al. |
| 6,149,623 | A | 11/2000 | Reynolds | 2003/0185895 A1 | 10/2003 | Lanphere et al. |
| 6,160,084 | A | 12/2000 | Langer et al. | 2003/0185896 A1 | 10/2003 | Buiser et al. |
| 6,162,377 | A | 12/2000 | Ghosh et al. | 2003/0187320 A1 | 10/2003 | Freyman |
| 6,165,193 | A | 12/2000 | Greene, Jr. et al. | 2003/0194390 A1 | 10/2003 | Krall et al. |
| 6,179,817 | B1 | 1/2001 | Zhong | 2003/0233150 A1 | 12/2003 | Bourne et al. |
| 6,191,193 | B1 | 2/2001 | Lee et al. | 2004/0076582 A1 | 4/2004 | Dimatteo et al. |
| 6,214,331 | B1 | 4/2001 | Vanderhoff et al. | 2004/0091543 A1 | 5/2004 | Bell et al. |
| 6,214,384 | B1 | 4/2001 | Pallado et al. | 2004/0092883 A1 | 5/2004 | Casey et al. |

| | | | |
|---|---|---|---|
| 2004/0096662 | A1 | 5/2004 | Lanphere et al. |
| 2004/0101564 | A1 | 5/2004 | Rioux et al. |
| 2004/0186377 | A1 | 9/2004 | Zhong et al. |
| 2005/0025800 | A1 | 2/2005 | Tan |
| 2005/0037047 | A1 | 2/2005 | Song |

FOREIGN PATENT DOCUMENTS

| | | |
|---|---|---|
| DE | 3834705 | 4/1990 |
| DE | 94 14 868.6 | 12/1994 |
| DE | 297 24 255 U1 | 10/2000 |
| DE | 100 26 620 | 3/2002 |
| EP | 0 067 459 | 12/1982 |
| EP | 0 122 624 | 10/1984 |
| EP | 0 123 235 | 10/1984 |
| EP | 0 243 165 | 10/1987 |
| EP | 0 294 206 | 12/1988 |
| EP | 0 402 031 | 12/1990 |
| EP | 0 422 258 | 4/1991 |
| EP | 0 458 079 | 11/1991 |
| EP | 0 458 745 | 11/1991 |
| EP | 0 470 569 | 2/1992 |
| EP | 0 547 530 | 6/1993 |
| EP | 0 600 529 | 6/1994 |
| EP | 0 623 012 | 11/1994 |
| EP | 0 706 376 | 4/1996 |
| EP | 0 730 847 | 9/1996 |
| EP | 0 744 940 | 12/1996 |
| EP | 0 764 047 | 3/1997 |
| EP | 0 797 988 | 10/1997 |
| EP | 0 993 337 | 4/2000 |
| ES | 2 096 521 | 3/1997 |
| JP | 59-196738 | 11/1984 |
| JP | 62-45637 | 2/1987 |
| JP | 4-74117 | 3/1992 |
| JP | 6-57012 | 3/1994 |
| JP | 9-110678 | 4/1997 |
| JP | 9-165328 | 6/1997 |
| JP | 9-316271 | 12/1997 |
| JP | 10-130329 | 5/1998 |
| JP | 2000189511 | 7/2000 |
| JP | 2001079011 | 3/2001 |
| JP | 2002-017848 | 1/2002 |
| NZ | 255409 | 2/1997 |
| NZ | 517377 | 8/2003 |
| TW | 421658 | 2/2001 |
| WO | WO 91/12823 | 5/1991 |
| WO | WO 92/21327 | 12/1992 |
| WO | WO 93/00063 | 1/1993 |
| WO | WO 93/19702 | 10/1993 |
| WO | WO 94/10936 | 5/1994 |
| WO | WO 95/03036 | 2/1995 |
| WO | WO 95/22318 | 8/1995 |
| WO | WO 95/33553 | 12/1995 |
| WO | WO 96/37165 | 11/1996 |
| WO | WO 96/39464 | 12/1996 |
| WO | WO 98/04616 | 2/1998 |
| WO | WO 98/10798 | 3/1998 |
| WO | WO 98/26737 | 6/1998 |
| WO | WO 98/47532 | 10/1998 |
| WO | WO 99/00187 | 1/1999 |
| WO | WO 99/12577 | 3/1999 |
| WO | WO 99/43380 | 9/1999 |
| WO | WO 99/51278 | 10/1999 |
| WO | WO 99/57176 | 11/1999 |
| WO | WO 00/23054 | 4/2000 |
| WO | WO 00/32112 | 6/2000 |
| WO | WO 00/40259 | 7/2000 |
| WO | WO 00/71196 | 11/2000 |
| WO | WO 00/74633 | 12/2000 |
| WO | WO 01/12359 | 2/2001 |
| WO | WO 01/66016 | 9/2001 |
| WO | WO 01/70291 | 9/2001 |
| WO | WO 01/72281 | 10/2001 |
| WO | WO 01/76845 | 10/2001 |
| WO | WO 01/93920 | 12/2001 |
| WO | WO 02/11696 | 2/2002 |
| WO | WO 02/34298 | 5/2002 |
| WO | WO 02/34299 | 5/2002 |
| WO | WO 02/34300 | 5/2002 |
| WO | WO 02/43580 | 6/2002 |
| WO | WO 03/016364 | 2/2003 |
| WO | WO 03/051451 | 6/2003 |
| WO | WO 03/082359 | 10/2003 |
| WO | WO 2004/019999 | 3/2004 |
| WO | WO 2004/073688 | 9/2004 |
| WO | WO 2004/075989 | 9/2004 |

OTHER PUBLICATIONS

Abrahams, J.M. et al., "Topic Review: Surface Modifications Enhancing Biological Activity of Guglielmi Detachable Coils in Treating Intracranial Aneurysms", Surg. Neurol. 54:34-41, 2000.

Abrahams, J.M. et al., "Delivery of Human Vascular Endothelial Growth Factor with Platinum Coils Enhances Wall Thickening and Coil Impregnation in a Rat Aneurysm Model", AJNR Am. J. Neuroradiol. 22:1410-1417, Aug. 2001.

Ahuja, A.A., "Platinum Coil Coatings to Increase Thrombogenicity: A Preliminary Study in Rabbits", ANJR Am. J. Neuroradiol. 14:794-798; Jul./Aug. 1993.

Antibody Labeling, http://www.altcorp.com/AffinityLabeling/ablaeling.htm, pp. 1-6, May 20, 2003.

Bachtsi, A.R. et al., "An Experimental Investigation of Enzyme Release from Poly(vinyl alcohol) crosslinked Microspheres", J. Microencapsulation, vol. 12, No. 1, pp. 23-35; 1995.

Barr, J.D., et al., "Polyvinyl Alcohol Foam Particles Sizes and Concentrations Injectable through Microcatheters", JVIR, vol. 9, No. 1, pp. 113-118; 1998.

Barton, P. et al., "Embolization of Bone Metastases," Journal of Vascular and Interventional Radiology, 7(1):81-88 (Jan.-Feb. 1996).

Battinelli, L. et al., "New Class of Poly(vinyl alcohol) Polymrs as Column-Chromatography Stationary Phases for Candida Rugosa Lipase Isoforms Separation", J. Chromatogr A, vol. 753, No. 1, pp. 47-55; 1996.

Beaujeux, R. et al., "Trisacryl Gelatin Microspheres for Therapeutic Embolization, II: Preliminary Clinical Evaluation in Tumors and Arteriovenous Malformations," AJNR Am. J. Neuroradiol., 17:541-548, Mar. 1996.

Berenstein, A. et al., "Catheter and Material Selection for Transarterial Embolization: Technical Considerations. II. Materials.", Radiology, vol. 132, No. 3, pp. 631-639; 1979.

Berenstein, A. et al., "Microembolization Techniques of Vascular Occlusion: Radiologic, Patohologic, and Clinical Correlation", AJNR Am I Neuroradiol, vol. 2, No. 3, pp. 261-267; 1981.

Berkowitz, R.P. et al., "Vaginal Expulsion of Submucosal Fibroids After Uterine Artery Embolization", Journal of Reproductive Medicine, vol. 44, No. 4, pp. 373-376; Apr. 1999.

Bourke et al., "Protein Drug Release from Photocrosslinked Poly(vinyl alcohol) Hydrogels," Society for Biomaterials 28th Annual Meeting Transactions, p. 144 (2002).

Bradley, E.A. et al., "Transcatheter Uterine Artery Embolisation to Treat Large Uterine Fibroids", British Journal of Obstetrics and Gynaecology, vol. 105, pp. 235-240; Feb. 1998.

Brockmann, J. et al., "Radiolabeling of p-Bz-DOTA-CD-11c antibody with 88Y: Conjugation, Labeling, Biodistribution studies", 2 pages, 2000 http://www.kernchemie.uni-mainz.de/downloads/jb2000/b14_brockmann.pdf.

Bruix, J. et al., "Transarterial Embolization Versus Symptomatic Treatment in Patients With Advanced Hepatocellular Carcinoma: Results of a Randomized, Controlled Trial in a Single Institution", Hepatology, Jun. 1998, vol. 27, No. 6, pp. 1578-1583, http://www.hepatitis-central.com/hcv/hcc/embolization/references.html.

Buhle, Jr. El, "Re: Re: Hepatic Arterial Embolization", UCLA Medicine Online, Mar. 10, 1996, http://www.meds.com/archive/mol-cancer/1996/msg00128.html, 2 pages.

Burczak, et al., "Long-term in vivo performance and biocompatibility of poly (vinyl alcohol) hydrogel macrocapsules for hybrid-type artificial pancreas", Biomaterials, vol. 17, No. 24, pp. 2351-2356, 1996.

Burczak, et al., "Polymeric materials for biomedical purposes obtained by radiation methods. V. hybrid artificial pancreas", Polim Med, vol. 24, No. 1-2, pp. 45-55, 1994 (English Summary included).

Capozza et al., "Endoscopic treatment of vesico-ureteric reflux and urinary incontinence: technical problems in the paediatric patient," British Journal of Urology, 75(4):538-542 (Apr. 1995).

Carroll, B.A. et al., "Microbubbles as Ultrasonic Contrast Agents", Investigative Radiology, vol. 14, No. 3, p. 374, Supplement to May-Jun. 1979.

Carroll, B.A. et al., "Gelatin Encapsulated Nitrogen Microbubbles as Ultrasonic Contrast Agents", Journal of Clinical and Laboratory Research, vol. 15, No. 1, pp. 260-266, Feb. 1980.

Carstensen, E.L. et al., "Determination of the Acoustic Properties of Blood and its Components", Journal of Acoustical Society of America, vol. 25, No. 2, pp. 286-289, Mar. 1953.

Choe, et al., "An experimental study of embolic effect according to infusion rate and concentration of suspension in transarterial particulate embolization", Invest Radiol, vol. 32, No. 5, pp. 260-270, 1997.

Chuang et al., "Experimental Canine Hepatic Artery Embolization with Polyvinyl Alcohol Foam Particles", Departments of Diagnostic Radiology and Veterinary Medicine, The University of Texas, M.D. Anderson Hospital and Tumor Institute at Houston, Texas, pp. 21-25, Oct. 1982.

Cirkel, U. et al., "Experience with Leuprorelin Acetate Depot in the Treatment of Fibroids: A German Multicentre Study", Clinical Therapeutics, vol. 14, Suppl. A, 1992.

Clarian Health Methodist—Indiana Lions Gamma Knife Center, "Arteriovenous Malformation," http://www.clarian.com/tyhealth/gammaknife/cond_arter.asp, 4 pages, Last Updated on Mar. 20, 2000.

Colombo M, "Treatment of Hepatocellular Carcinoma", Journal of Viral Hepatitis, 4(Suppl. 1):125-130 (1997), http://home.texoma.net/~moreland/stats/hcc-9.html.

Concentric Medical, Inc.- Product Information (3 pages), 2002.

Cruise et al., "In Vitro and In Vivo Characterization of a Hydrogel-Based Aneurysm Embolization System," Society for Biomaterials 28th Annual Meeting Transactions, p. 203 (2002).

Deasy, P. B., "Microencapsulation and Related Drug Processes", New York, NY, Marcel Dekker, Inc., 345 pages, 1984 (Table of Contents only).

de Gast, A.N. et al., "Transforming Growth Factor β-coated Platinum Coils for Endovascular Treatment of Aneurysms: An Animal Study", Neurosurgery, vol. 49, No. 3, pp. 690-696, Sep. 2001.

Derdeyn, et al., "Collagen-coated acrylic microspheres for embolotherapy: in vivo and in vitro characteristics", American Journal of Neuroradiology, vol. 18, No. 4, pp. 647-653, 1997.

Derdeyn, et al., "Polyvinyl alcohol particle size and suspension characteristics", American Journal of Neuroradiology, vol. 16, pp. 1335-1343, 1995.

DiLuccio et al., "Sustained-Release Oral Delivery of Theophylline by Use of Polyvinyl Alcohol and Polyvinyl Alcohol-Methyl Acrylate Polymers", Journal of Pharmaceutical Sciences, vol. 83, No. 1, pp. 104-106, Jan. 1994.

Duckwiler et al., "Catheters, embolic agents spark neurointervention," Diagnostic Imaging, 16(5):66-72 (May 1994).

Ersek et al., "Bioplastique: A New Textured Copolymer Microparticle Promises Permanence in Soft-Tissue Augmentation," Plastic and Reconstructive Surgery, 87(4):693-702 (Apr. 1991).

Eskridge, "Interventional Neuroradiology," Radiology, 172:991-1006 (Nov. 1989).

Feldman, L. et al., "Transcatheter Vessel Occlusion: Angiographic Results Versus Clinical Success", Radiology, vol. 147, pp. 1-5, Apr. 1983.

Ferrofluids, Physical Properties and Applications, Ferrofluidics Corp., Nashua, NH, 5 pages, 1986.

FeRx Incorporated, FERX Profile, http://www.biotechshares.com/FERX.htm, 4 pages (Retrieved from the internet on Jun. 26, 2003).

"Fibroid Treatment Collective—Fibroid Embolization," 2 pages, http://www.fibroids.org.

Fritzsch, T. et al., "SH U 508, A Transpulmonary Echocontrast Agent", Investigative Radiology, vol. 25, Supplement 1, pp. S160-S161, Sep. 1990.

Fujimoto, S. et al., "Biodegradable Mitomycin C Microspheres Given Intra-Arterially for Inoperable Hepatic Cancer", Cancer, vol. 56, pp. 2404-2410, 1985.

Gander, et al., "Effect of polymeric network structure on drug release from cross-linked poly(vinyl alcohol) micromatrices", Pharm Res, vol. 6, No. 7, pp. 578-584, 1989.

Germano, et al., "Histopathological follow-up study of 66 cerebral arteriovenous malformations after therapeutic embolization with polyvinyl alcohol", J Neurosurg, vol. 76, No. 4, pp. 607-614, 1992.

Geschwind et al., "Chemoembolization of Liver Tumor in a Rabbit Model: Assessment of Tumor Cell Death with Diffusion-Weighted MR Imaging and Histologic Analysis", Journal of Vascular and Interventional Radiology, vol. 11, No. 10, pp. 1244-1255, Dec. 2000.

Gilbert, W.M. et al., "Angiographic Embolization in the Management of Hemorrhagic Complications of Pregnancy", American Journal of Obstetrics and Gynecology, vol. 166, No. 2, pp. 493-497, Feb. 1992.

Gohel, et al., "Formulation design and optimization of modified-release microspheres of diclofenac sodium", Drug Dev Ind Pharm, vol. 25, No. 2, pp. 247-251, 1999.

Goldberg, B.B., "Ultrasonic Cholangiography", Radiology, vol. 118, pp. 401-404, Feb. 1976.

Goodwin, et al., "Overview of embolic agents and their indications", Eleventh Annual International Symposium on Endovascular Therapy, pp. 303-306, 1999.

Goodwin, et al., "Preliminary experience with uterine artery embolization for uterine fibroids", Journal of Vascular and Interventional Radiology, vol. 8, No. 4, pp. 517-526, 1997.

Gramiak et al., "Echocardiography of the Aortic Root," Investigative Radiology, 3(5):356-366 (Sep.-Oct. 1968).

Gramiak, R. et al., "Ultrasound Cardiography: Contrast Studies in Anatomy and Function", Radiology, vol. 92, No. 5, pp. 939-948, Apr. 1969.

Grandfils, et al., "Preparation of poly (D,L) lactide microspheres by emulsion solvent evaporation, and their clinical implications as a convenient embolic material", J Biomed Mater Res, vol. 26, No. 4, pp. 467-479, 1992.

Greenwood, L.H. et al., "Obstetric and Nonmalignant Gynecologic Bleeding: Treatment with Angiographic Embolization", Radiology, vol. 164, No. 1, pp. 155-159, Jul. 1987.

Gupta et al., "Plasma-induced graft polymerization of acrylic acid onto poly(ethylene terephthalate) films: characterization and human smooth muscle cell growth on grafted films," Biomaterials, 23:863-871 (2002).

Halstenberg et al., "Biologically Engineered Protein-graft-Poly(ethylene glycol) Hydrogels: A Cell Adhesive and Plasmin-Degradable Biosynthetic Material for Tissue Repair," Biomacromolecules, 3(4):710-723 (2002).

Hamada et al., "Embolization with Cellulose Porous Beads, II: Clinical Trial," AJNR Am. J. Neuroradiol., 17:1901-1906 (Nov. 1996).

Hirano et al., "Transcutaneous Intrafold Injection For Unilateral Vocal Fold Paralysis: Functional Results," Ann. Otol. Rhinol Laryngol., 99(8):598-604 (Aug. 1990).

Horak et al., "Hydrogels in endovascular embolization. I. Spherical particles of poly (2-hydroxyethylmethacrylate) and their medico-biological properties", Biomaterials, 7(3):188-192 (May 1986).

Horak et al., "Hydrogels in endovascular embolization. II. Clinical use of spherical particles", Biomaterials, 7(6):467-470 (Nov. 1986).

Huang et al., "Percutaneous endovascular embolization of intracerebral arteriovenous malformations. Experience in 72 cases", Chin Med J, vol. 108, No. 6, pp. 413-419, 1995.

"Injectable Tissue Implant Could Repair Ravages of Surgery", Clemson University, Biotech Week, Oct. 22, 2003, p. 117.

Jack, et al., "Radiolabeled polyvinyl alcohol particles: a potential agent to monitor embolization procedures", Int J Rad Appl Instrum B, vol. 13, No. 3, pp. 235-243, 1986.

Jiaqi, Y. et al., "A New Embolic Material: Super Absorbent Polymer (SAP) Microsphere and Its Embolic Effects," Nippon Acta Radiologica, 56:19-24 (1996) (English Abstract included).

Jones, S.K. et al., "Experimental Examination of a Targeted Hyperthermia System Using Inductively Heated Ferromagnetic Microspheres in Rabbit Kidney", Phys. Med. Biol., vol. 46, No. 2, pp. 385-398, Feb. 2001, www.iop.org/Journals/pb.

Joy C, et al., "Use of Preoperative Embolization in the Treatment of Vascular Metastatic Lesions of the Spine," http://www.aaos.org/wordhtml/anmeet91/scipro/ppr472.htm, Mar. 12, 1991.

Jung et al., "Sulfobutylated poly(vinyl alcohol)-graft-poly(lactide-co-glycolide)s facilitate the preparation of small negatively charged biodegradable nanospheres," Journal of Controlled Release, 67:157-169 (2000).

Kai, et al., "The utility of the microcrystalline cellulose sphere as a particulate embolic agent: an experimental study", American Journal of Radiology, vol. 21, No. 6, pp. 1160-1163, 2000.

Kallmes, D.F. et al., "In Vitro Proliferation and Adhesion of Basic Fibroblast Growth Factor-producing Fibroblasts on Platinum Coils", Radiology, vol. 206, No. 1, pp. 237-243, Jan. 1998.

Kan, et al., "In vivo microscopy of the liver after injection of lipiodol into the hepatic artery and portal vein in the rat", Acta Radiologica, vol. 30, pp. 419-425, 1989.

Kerber, C., "Balloon Catheter with a Calibrated Leak", Radiology, vol. 120, pp. 547-550, Sep. 1976.

Kerber et al., "Polyvinyl Alcohol Foam: Prepackaged Emboli for Therapeutic Embolization", American Journal Roentgenol, vol. 130, pp. 1193-1194, Jun. 1978.

Kerber, "Flow-Controlled Therapeutic Embolization: A Physiologic and Safe Technique", AJR, vol. 134, pp. 557-561, Mar. 1980.

Khankan et al., "Embolic Effects of Superabsorbent Polymer Microspheres in Rabbit Renal Model: Comparison with Tris-acryl Gelatin Microspheres and Polyvinyl Alcohol," Radiation Medicine, 22(6):384-390 (2004).

Kim, et al., "Composite poly(vinyl alcohol) beads for controlled drug delivery", Pharm Res, vol. 9, No. 1, p. 10-16, 1992.

Kim et al., "Hollow Silica Spheres of Controlled Size and Porosity by Sol-Gel Processing," J. Am. Ceram. Soc., 74(8):1987-1992 (Aug. 1991).

Kim et al., "Poly(vinyl alcohol) beads with core-shell structure for drug delivery," Cosmetic and Pharmaceutical Applications of Polymers, Plenum Press, New York, pp. 209-214 (1991).

Kim et al., "Suspension polymerized poly(vinyl alcohol) beads for drug delivery," Polymeric Materials: Science and Engineering, Proceedings of the ACS Division of Polymeric Materials: Science and Engineering, 63:64-67 (1990).

Kochan, J.P. et al., "Interventional Neuroradiology: Current Practices and Techniques at Temple University Hospital," http://www.temple.edu/radiology/stroke.html, 5 pages.

Krinick et al., "A polymeric drug delivery system for the simultaneous delivery of drugs activatable by enzymes and/or light," J. Biomater. Sci. Polymer Edn, 5(4):303-324 (1994).

Kuhn, R. et al., "Embolic Occlusion of the Blood Supply to Uterine Myomas: Report of 2 Cases", Aust. NZ. J. Obstet. Gynaecol., vol. 39, No. 1, pp. 120-122, Feb. 1999.

Kurata, et al., "Preoperative embolization for meningiomas using PVA particles", No Shinkei Geka, vol. 20, No. 4, pp. 367-373, 1992 (English Abstract included).

Kurbatova, G.T. et al., "Magnetically-guided Anesthetics Based on Highly Dispersed Iron Powders Coated by Polyacrylamide", Biofizika, vol. 47, No. 2, pp. 331-337, Mar.-Apr. 2002, http://intapp.medscape.com/px/medlineapp (English Abstract included).

Kurosaki et al., "Evaluation of PVA-Gel Spheres as GI-Transit Time Controlling Oral Drug Delivery System", Proceedings of the 19th International Symposium on Controlled Release of Bioactive Materials, Orlando, Florida, pp. 273-274, Jul. 26-31, 1992.

Kusano, et al., "Low-dose particulate polyvinylalcohol embolization in massive small artery intenstinal hemorrahage. Experimental and clinical results", Invest Radiol, vol. 22, No. 5, pp. 388-392, 1987.

Labarre et al., "Complement activation by substituted polyacrylamide hydrogels for embolisation and implantation", Biomaterials, vol. 23, pp. 2319-2327, 2002.

Lammer, et al., "Transcatheteral embolization with polyvinyl alcohol—technic and experimental studies", Rontgenblatter, vol. 36, No. 1, pp. 10-14, 1983 (English Abstract included).

Latchaw et al., "Polyvinyl Foam Embolization of Vascular and Neoplastic Lesions of the Head, Neck, and Spine", Radiology, vol. 131, pp. 669-679, Jun. 1979.

Laurent, "Materials and biomaterials for interventional radiology," Biomed. & Pharmacother., 52:76-88 (1998).

Lemperle et al., "PMMA Microspheres for Intradermal Implantation: Part I. Animal Research," Annals of Plastic Surgery, 26(1):56-63 (Jan. 1991).

Lendlein, A. et al., "Biodegradable, Elastic Shape-Memory Polymers for Potential Biomedical Applications", Science, vol. 296, pp. 1673-1676, May 31, 2002.

Leung et al., "Determinants of Postembolization Syndrome after Hepatic Chemoembolization", Journal of Vascular and Interventional Radiology, vol. 12, No. 3, pp. 320-326, Mar. 2001.

Leventon, William, "Hemocompatible Coatings for Blood-Contacting Devices", Medical Device & Diagnostic Industry: Coating Technologies—New Methods to Ensure Blood Compatibility, vol. 25, No. 8, pp. 62-67, Aug. 2003.

Levy et al., "Transcatheter Uterine Artery Embolization for the Treatment of Symptomatic Uterine Fibroid Tumors," Journal of Women's Imaging, 2(4):168-175 (2000).

Lipman, "Uterine artery embolization for the treatment of symptomatic uterine fibroids: A review," Applied Radiology, 29(7):15-20 (Jul. 2000).

Lowery, C.L. et al., "Screening Tests for Intrauterine Growth Retardation: A Comparison of Umbilical Artery Doppler to Real-Time Ultrasound", Echocardiography, vol. 7, No. 2, pp. 159-164, Mar. 1990.

Marich, K.W. et al., "Real-Time Imaging with a New Ultrasonic Camera: Part I, In Vitro Experimental Studies on Transmission Imaging of Biological Structures", Journal of Clinical Ultrasound, vol. 3, No. 1, pp. 5-16, Mar. 1975.

Markoff, et al., "Uterine arteriovenous malformation successfully embolized with a liquid polymer, isobutyl 2-cyanoacrylate", Am. J. Obstet. Gynecol., 155:659-660 (Sep. 1986).

Markus et al., "Experimental Aspects of High-Intensity Transient Signals in the Detection of Emboli," J. Clin. Ultrasound., 23(2):81-87 (Feb. 1995).

Maruhashi, "Modified Polyvinyl Alcohols I and II," Polyvinyl Alcohol—Developments, John Wiley & Sons, Chichester, England, pp. 160-161 and pp. 186-191 (1992).

Marx, W. F. et al., "Endovascular Treatment of Experimental Aneurysms by Use of Biologically Modified Embolic Devices: Coil-mediated Intraaneurysmal Delivery of Fibroblast Tissue Allografts", AJNR. Am. J. Neuroradiol., vol. 22, pp. 323-333, Feb. 2001.

Mather, P.T., Research Group Homepage, Basic Goals and Methods, http://www.ims.uconn.edu/~mather, 4 pages.

Matsumaru, et al., "Embolic materials for endovascular treatment of cerebral lesions", J Biomater Sci Polym Ed, vol. 8, No. 7, pp. 555-569, 1997.

Matsumoto, H. et al., "Basic Fibroblast Growth Factor Released from a Platinum Coil with a Polyvinyl Alcohol Core Enhances Cellular Proliferation and Vascular Wall Thickness: An In Vitro and In Vivo Study", Neurosurgery, vol. 53, No. 2, pp. 402-408, Aug. 2003.

Matsumoto, Y. et al., "Room-Temperature Ferromagnetism in Transparent Transition Metal-Doped Titanium Dioxide", Science, vol. 291, pp. 854-856, Feb. 2, 2001, www.sciencemag.org.

Mavligit, G. et al., "Gastrointestinal Leiomyosarcoma Metastatic to the Liver," Cancer, 75(8):2083-2088 (Apr. 15, 1995).

McIvor, J. et al., "Pregnancy After Uterine Artery Embolization to Control Haemorrhage from Gestational Trophoblastic Tumour", British Journal of Radiology, vol. 69, No. 823, pp. 624-629, Jul. 1996.

MerocelXL Sponge with Hytrol, http://www.xomed.com/newproducts/merocelxl/merocelxl_earwick.asp, 3 pages, 2001.

Mid-America Interventional Radiological Society, "New Treatment for Uterine Fibroids Avoids Surgery," http://www.mirs.org/fibroids.htm, 6 pages, Submitted in Oct. 1999.

Moroz, P. et al., "Arterial Embolization Hyperthermia in Porcine Renal Tissue", Journal of Surgical Research, vol. 105, No. 2, pp. 209-214, Jun. 15, 2002.

Moroz, P. et al., "Hepatic Clearance of Arterially Infused Ferromagnetic Particles", Int. J. Hyperthermia, vol. 19, No. 1, pp. 23-24, Feb. 2003, http://www.tandf.co.uk./journals.

Nakabayashi, et al., "Evaluation of particulate embolic materials with MR imaging, scanning electron microscopy, and phase-contrast microscopy", American Journal of Neuroradiology, vol. 18, No. 3, pp. 485-491, 1997.

Nakstad, et al., "Embolization of intracranial arteriovenous malformations and fistulas with polyvinyl alcohol particles and platinum fibre coils", Neuroradiology, vol. 34, No. 4, pp. 348-351, 1992.

Namiki, "Application of Teflon Paste for Urinary Incontinence—Report of 2 Cases," Uro. Int., 39:280-282 (1984).

Nash, et al., "Modifications of polystyrenic matrices for the purification of proteins. II. Effect of the degree of glutaraldehyde-poly(vinyl alcohol) crosslinking on various dye ligand chromatography systems", J Chromatogr A, vol. 776, No. 1, pp. 55-63, 1997.

Nikishin LF et al., "Interventional radiology in diffuse toxic goiter", European Congress of Radiology, Abstract 9041, 1999, http://www.ecr.org/conferences/ecr1999/sciprg/abs/p090041.htm, 7 pages.

Ophir, et al., "Ultrasonic backscatter from contrast producing collagen microspheres", Ultrasonic Imaging, vol. 2, pp. 67-77, 1980.

Oregon Health Sciences University, "Fibroid Embolization," http://www.uhmc.edu/dotter-fibroid, 34 pages.

Orienti et al., "Crosslinked Polyvinylalcohol Hydrogels as Vehicles for Hydrophilic Drugs," Arch. Pharm. Pharm. Med. Chem., 333:421-424 (2000).

Orsini, L. F. et al., "Pelvic Organs in Premenarcheal Girls: Real-Time Ultrasonography", Radiology, vol. 153, No. 1, pp. 113-116, Oct. 1984.

Parker, et al., "A particulate contrast agent with potential for ultrasound imaging of liver", Ultrasound in Medicine and Biology, vol. 13, No. 9, pp. 555-566, 1987.

Pedley et al., "Hydrogels in Biomedical Applications," British Polymer Journal, 12:99-110 (Sep. 1980).

Pesant A.C. et al., "Dural fistulas involving the cavernous sinus: Treatment by embolization—7 cases", European Congress of Radiology, Abstract 3-088, 1997, http://www.ecr.org/conferences/ecr1997/sciprg/abs/9703088p.htm, 1 page.

Phillips, D. R. et al., "Experience with Laparoscopic Leiomyoma Coagulation and Concomitant Operative Hysteroscopy", J. Am. Assoc. Gynecol. Laparosc, vol. 4, No. 4, pp. 425-533, Aug. 1997.

Physicians' Desk Reference Family Guide to Women's Health, "Chapter 7—Common Disorders of the Reproductive System," http://www.healthsquare.com/pdrfg/wh/chapters/wh1ch01.htm, 24 pages.

Pistel et al., "Brush-like branched biodegradable polyesters, part III Protein release from microspheres of poly(vinyl alcohol)-graft-poly(D,L-lactic-co-glycolic acid)," Journal of Controlled Release, 73:7-20 (2001).

Politano et al., "Periurethral Teflon Injection for Urinary Incontinence," The Journal of Urology, 111:180-183 (1974).

Poppe, W. et al., "Pregnancy after Transcatheter Embolization of a Uterine Arteriovenous Malformation", Am. J. Obstet. Gynecol., vol. 156, No. 5, pp. 1179-1180, May 1987.

Pritchard, et al., "Poly(Vinyl Alcohol): Basic Properties and Uses", London, England: Gordon and Breach Science Publishers, pp. 95-97, 1970.

Progelhof et al., "Table 4.21. Properties of electrical insulating films (101)," Polymer Engineering Principles: Properties, Processes, and Tests for Design, Hanser Publishers, Munich, p. 383 (1993).

Pryor J. and Berenstein A., "Epistaxis (Nose-bleeds)," http://www.wehealny.org/inn/Radiology/nosebleeds.html, 1 page.

"Pulmonary artery pseudoaneurysm/aneurysm," http://www.mamc.amedd.army.mil/williams/chest/vascular/paaneurysm/paaneyrysm.htm, 2 pages.

Purdy, et al., "Arteriovenous malformations of the brain: choosing embolic materials to enhance safety and ease of excision", J Neurosug, vol. 77, No. 2. pp. 217-222, 1992.

PVA Plus, AngioDynamics® Inc., "Reliable PVA Foam Formulated for Consistency and Controlled Delivery—Embolization Particles Ordering Information," www.angiodynamics.com, 2 pages (Aug. 2002).

Quisling, et al., "Histopathology analysis of intraarterial polyvinyl alcohol microemboli in rat cerebral cortex", American Journal of Neuroradiology, vol. 5, pp. 101-104, 1984.

Rajan et al., "Sarcomas Metastatic to the Liver: Response and Survival after Cisplatin, Doxorubicin, Mitomycin-C, Ethiodol, and Polyvinyl Alcohol Chemoembolization", Journal of Vascular and Interventional Radiology, vol. 12, No. 2, pp. 187-193, Feb. 2001.

Ramos, et al., "Tumor vascular signals in renal masses: detection with Doppler US", Radiology, vol. 168, No. 3, pp. 633-637, 1988.

Ravina, J.H. et al., "Advantage of Pre-Operative Embolization of Fibroids: About a Multicentric Set of 31 Cases", Contracept. Fertil. Sex., vol. 23, No. 1, pp. 45-49, Jan. 1995 (English Abstract included).

Ravina, J.H. et al., "Arterial Embolisation to Treat Uterine Myomata", Lancet, vol. 346, pp. 671-674, Sep. 9, 1995.

Ravina, J.H. et al., "Interest of Particulate Arterial Embolization in the Treatment of Some Uterine Myoma", Bull. Acad. Natle. Med., vol. 181, No. 2, pp. 233-246, Feb. 4, 1997 (English Summary included).

Repa, I. et al., "Mortalities Associated with Use of a Commercial Suspension of Polyvinyl Alcohol," Radiology, 170(2):395-399 (Feb. 1989).

Rhine et al., "Polymers for Sustained Macromolecule Release: Procedures to Fabricate Reproducible Delivery Systems and Control Release Kinetics," Journal of Pharmaceutical Sciences, 69(3):265-270 (Mar. 1980).

Rump, A. et al., "Pharmacokinetics of Intraarterial Mitomycin C in the Chemoembolisation Treatment of Liver Metastases," Gen. Pharmac., 27(4):669-671 (1996).

Schetky, "Shape-Memory Alloys," Encyclopedia of Chemical Technology, Third Edition, vol. 20, John Wiley & Sons, New York, pp. 726-736 (1982).

Schlief, R. et al., "Enhanced Color Doppler Echocardiography of the Left Heart After Intravenous Injection of a New Saccharide Based Agent in Humans", Circulation, vol. 82, No. 2, p. 28, Oct. 1990 (Abstract).

Schlief, R. et al., "Successful Opacification of the Left Heart Chamber on Echocardiographic Examination after Intravenous Injection of a New Saccharide Based Contrast Agent", Echocardiography, vol. 7, No. 1, pp. 61-64, Jan. 1990.

Schwarz et al., "The acoustic filter: An ultrasonic blood filter for the heart-lung machine," J. Thorac. Cardiovasc. Surg., 104(6):1647-1653 (Dec. 1992).

Shafik, "Intraesophageal Polytef injection for the treatment of reflux esophagitis," Surg. Endosc., 10:329-331 (1996).

Shape Shifters, http://www.sciam.com/tehbiz/0501scicit6.html, 3 pages, 2001.

Shung, K.K. et al., "Scattering of Ultrasound by Blood", IEEE Transactions on Biomedical Engineering, vol. BME-23, No. 6, pp. 460-467, Nov. 1976.

Sigelmann, R.A. et al., "Analysis and Measurement of Ultrasound Backscattering from an Ensemble of Scatters Excited by Sine-Wave Bursts", Journal of Acoustical Society of America, vol. 53, No. 4, pp. 1351-1355, Apr. 1973.

SIR-Spheres (Yttrium-90 Microspheres), pp. 1-12.

SIR-Spheres, Radioactive Implant (Yttrium-90 Microspheres), Sirex Medical, Inc., San Diego, CA, Nov. 6, 2000, pp. 1-15.

Sirtex Medical Limited—Product Description, http://www.sirtex.com/?p=72, 3 pages (Retrieved from the internet on May 27, 2003).

Sirtex Medical Limited—Targeted Radiotherapy with SIR-Spheres, http://www.sirtex.com/?p=57, 2 pages (Retrieved from the internet on May 27, 2003).

Siskin et al., "Pathologic Evaluation of a Spherical Polyvinyl Alcohol Embolic Agent in a Porcine Renal Model," J. Vasc. Interv. Radiol., 14:89-98 (2003).

Skotland, T. et al., "In Vitro Stability Analyses as a Model for Metabolism of Ferromagnetic Particles (Clariscan3), a Contrast Agent for Magnetic Resonance Imaging", J. Pharm. Biomed. Anal., vol. 28, No. 2, pp. 323-329, Apr. 15, 2002.

"Smart Sutures Tie Themselves", Apr. 26, 2002, http://www.sciam.com/article.cfm?articleID=00047706-121F-1CD0-B4A8809EC588, 2 pages.

Smith et al., *"Evaluation of Polydimethylsiloxane as an alternative in the Endoscopic Treatment of Vesicoureteral Reflux," The Journal of Urology*, 152:1221-1224 (Oct. 1994).

Smith et al., "Left Heart Opacification with Peripheral Venous Injection of a New Saccharide Echo Contrast Agent in Dogs", JACC, vol. 13, No. 7, pp. 1622-1628, Jun. 1989.

Soppimath et al., "Controlled release of antihypertensive drug from the interpenetrating network poly(vinyl alcohol)-guar gum hydrogel microspheres," J. Biomater. Sci. Polymer Edn, 11(1):27-43 (2000).

Spickler, et al., "The MR appearance of endovascular embolic agents in vitro with clinical correlation", Comput Med Imaging Graph, vol. 14, No. 6, pp. 415-423, 1990.

Spies JB, "Georgetown University Medical Center. Uterine Fibroid Embolization (UFE). An alternative to surgery for patients with uterine fibroids. Literature Review," http://www.fibroidoptions.com/pr-lit.htm, 6 pages, Sep. 1, 2001.

Stancato-Pasik, A. et al., "Obstetric Embolotherapy: Effect on Menses and Pregnancy", Radiology, vol. 204, No. 3, pp. 791-793, Sep. 1997.

Stein, R. et al., "Targeting Human Cancer Xenografts with Monoclonal Antibodies Labeled Using Radioiodinated, Diethylenetriaminepentaacetic Acid-appended Peptides", Clinical Cancer Research, vol. 5, No. 10, pp. 3079-3087, Oct. 1999 (Supplement).

Strasnick et al., "Transcutaneous Teflon® Injection for Unilateral Vocal Cord Paralysis: An Update," The Laryngoscope, 101:785-787 (Jul. 1991).

Stridbeck, H. et al, "Collateral Circulation Following Repeated Distal Embolization of the Hepatic Artery in Pigs," Invest. Radiol., 19(3):179-183 (1984).

Strunk, et al., "Treatment of congenital coronary arteriovenous malformations with microparticle embolization", Cathet Cardiovasc Diagn, vol. 22, No. 2, pp. 133-136, 1991.

Swanson DA et al., "The role of embolization and nephrectomy in the treatment of metastatic renal carcinoma", Urologic Clinics of North America, 7(3):719-730, 1980. University of Pennsylvania Cancer Center—Oncolink, http://www.oncolink.upenn.edu/pdg_html/cites/00/00585.html.

Tabata et al., "Tumor accumulation of poly(vinyl alcohol) of different sizes after intravenous injection", Journal of Controlled Release, vol. 50, pp. 123-133, Jan. 2, 1998.

Tadavarthy et al., "Polyvinyl Alcohol (Ivalon)—A New Embolic Material", The American Journal of Roentgenology Radium Therapy and Nuclear Medicine, vol. 125, No. 3, pp. 609-616, Nov. 1975.

Tadavarthy et al., "Polyvinyl Alcohol (Ivalon) as an Embolizing Agent", Seminars in Interventional Radiology, vol. 1, No. 2, pp. 101-109, Jun. 1984.

Tamatani, S. et al., "Histological Interaction of Cultured Endothelial Cells and Endovascular Embolic Materials Coated with Extracellular Matrix", J. Neurosurg., vol. 86, No. 1, pp. 109-112, Jan. 1997.

Tao, et al., "Study of microspheres for embolization of hepatic artery", Acta Pharmaceutica Sinica, vol. 23, No. 1, pp. 55-60, 1988.

Tao, at al., "Study of microspheres for embolization of hepatic artery", (Translation) Acta Pharmaceutica Sinica, vol. 23, No. 1, pp. 55-60, 1988.

Terada, et al., "Preoperative embolization of meningiomas fed by ophthalmic branch arteries", Surg. Neurol, vol. 45, No. 2, pp. 161-166, 1996.

Thanoo, et al., "Controlled release of oral drugs from cross-linked polyvinyl alcohol microspheres", J Pharm Pharmacol, vol. 45, No. 1, pp. 16-20, 1993.

Thanoo, B. C. et al., "Preparation and Properties of Barium Sulphate and Methyl Iothalamate Loaded Poly(vinyl Alcohol) Microspheres as Radiopaque Particulate Emboli," Journal of Applied Biomaterials, 2:67-72 (1991).

Thanoo, et al., "Tantalum loaded silicone microspheres as particulate emboli", J Microencapsul, vol. 8, No. 1, pp. 95-101, 1991.

Thelen, V.M. et al., "Catheter Embolisation of Metastasising Renal Carcinoma Using Butyle-2-cyano-acrylate", Fortschr. Rontgenstr., vol. 124, No. 3, pp. 232-235, Mar. 1976 (English Abstract included).

The Fibroid Embolization Center of the New York United Hospital Medical Center, "Fibroid Facts," http://www.uhmc.com/fibro2.htm, 9 pages.

The Vanderbilt-Ingram Cancer Center, "Kidney Cancer," http://www.mc.Vanderbilt.Edu/cancer/cancerinfo/kidney.html, 1 page, 2001.

Tian et al., "Design and synthesis of amphiphilic poly (ethylene glycol) derivatives as micellar drug delivery systems," Polymer Preprints, 43(2):719-720 (Fall 2002).

Tikkakoski, et al., "Preoperative embolization in the management of neck paragangliomas", Laryngoscope, vol. 107, pp. 821-826, 1997.

Toon, "Improving a Key Weapon Against Cancer," Research Horizons, pp. 11-12, Spring/Summer 2001.

Touho, et al., "Intravascular treatment of spinal arteriovenous malformations using a microcatheter—with special reference to serial xylocaine tests and intravascular pressure monitoring", Surgical Neurology, vol 42, No. 2, pp. 148-156, 1994.

UCLA Radiological Sciences, "A summary of terms appearing in this text," http://www.radsci.ucla.edu:8000/aneurysm/terms.html, 1 page.

University Medical Center SUNY Stony Brook, Department of Urology, "Variococele and its treatment," http://www.hsc.sunysb.edu/urology/male_inf...variocoele_and_its_treatment.html, 8 pages, Last Updated on Mar. 12, 2001.

Vivas S et al., "Arterioportal fistula and hemobilia in a patient with hepatic transplant", Gastroenterol Hepatol, 21(2):88-9, http://www.doyma.es/copiani/revistas/gastro/abstr/abs_p080.html, Feb. 1998 (English Abstract included).

Vogel F, "Nonsurgical Management of Uterine Fibroids," http://www.holyname.org/brochure/fibroids.html, 5 pages.

Wakhloo, et al., "Extended preoperative polyvinyl alcohol microembolization of intracranial meningiomas: Assessment of two embolization techniques", American Journal of Neuroradiology, vol. 14, pp. 571-582, 1993.

Walker WJ, "Non Surgical Treatment of Fibroids in the UK by Uterine Artery Embolisation—An Alternative to Hysterectomy, Myomectomy and Myolysis," http://www.fibroids.co.uk/thepaper.html, 2 pages, 2002.

Walsh RM et al., "Role of Angiography and Embolization for Acute Massive Upper Gastronintestinal Hemorrhage," J. Gastrointest. Surg., 3:61-66 (1999).

Waltman, A.C. et al., "Technique for Left Gastric Artery Catheterization", Radiology, vol. 109, No. 3, pp. 732-734, Dec. 1973.

White, Jr., "Embolotherapy in Vascular Disease," American Journal of Roentgenology, 142:27-30 (Jan. 1984).

Widder, K.J. et al., "Selective Targeting of Magnetic Microspheres Containing Adriamycin: Total Remission in Yoshida Sarcoma-Bearing Rats", Proceedings of the 16th Annual Meeting of American Society of Clinical Oncology, May 26-27, 1980, San Diego, CA, p. 261.

Widder, K. et al., "Magnetic Microspheres: Synthesis of a Novel Parenteral Drug Carrier", Journal of Pharmaceutical Sciences, vol. 68, No. 1, pp. 79-82, Jan. 1979.

Wikholm G et al., "Embolization of Cerebral Arteriovenous Malformations: Part I—Technique, Morphology, and Complications", Neurosurgery, 39(3):448-459 (Sep. 1996).

Winters et al., "Periurethral injection of collagen in the treatment of intrinsic sphincteric deficiency in the female patient," The Urologic Clinics of North America, 22(3):673-678 (Aug. 1995).

Worthington-Kirsch RL, "Interventionalists offer management option for uterine fibroids," Diagnostic Imaging, 21(3):47-49, Mar. 1999, http://www.dimag.com/references/9903wortrefs.html.

Worthington-Kirsch, et al., "Uterine arterial embolization for the management of leiomyomas: Quality-of-life assessment and clinical response", Radiology, vol. 208, No. 3, 625-629, 1998.

Wright, K.C. et al., "Partial Splenic Embolization Using Polyvinyl Alcohol Foam, Dextran, Polystyrene, or Silicone," Radiology, 142:351-354, Feb. 1982.

Wu, A.M., "Engineered Antibodies for Breast Cancer Imaging and Therapy," http://www.cbcrp.org/research/PageGrant.asp?grant_id=111, 3 pages, 1996.

Yamada, T. et al., "Extended Intraarterial Cisplatin Infusion for Treatment of Gynecologic Cancer After Altercation of Intrapelvic Blood Flow and Implantation of a Vascular Access Device", Cardiovasc. Intervent. Radiol., vol. 19, pp. 139-145, 1996.

Yamashita, Y. et al., "Transcatheter Arterial Embolization of Obstetric and Gynaecological Bleeding: Efficacy and Clinical Outcome", British Journal of Radiology, vol. 67, pp. 530-534, Jun. 1994.

Yoon et al., "Surface Immobilization of Galactose onto Aliphatic Biodegradable Polymers for Hepatocyte Culture," Biotechnol. Bioeng., 78(1):1-10 (Apr. 5, 2002).

Yusi et al., "Submuscosal Injection of Polyvinyl Alcohol in Artificially Created Vesico-Ureteral Reflux: A Preliminary Report," Asian J. Surg., 18(2):122-127 (Apr. 1995).

Zisch et al., "Covalently conjugated VEGF-fibrin matrices for endothelialization," Journal of Controlled Release, 72:101-113 (2001).

Ziskin, M.C. et al., "Contrast Agents for Diagnostic Ultrasound", Investigative Radiology, vol. 7, No. 6, pp. 500-505, Nov.-Dec. 1972.

Zou, Ying-hua, et al. "Experimental Canine Hapatic Artery Embolization with Polyvinyl Alcohol Microspheres," Zhong Hua Fang-She Xue ZaZhi, 23(6):330-332 (1989).

Zou, Ying-hua, et al. "Experimental Canine Hapatic Artery Embolization with Polyvinyl Alcohol Microspheres," Translation, Zhong Hua Fang-She Xue ZaZhi, 23(6):330-332 (1989).

Abbara et al., "Transcervical Expulsion of a Fibroid as a Result of Uterine Artery Embolization for Leiomyomata", JVIR, vol. 10, No. 4, pp. 409-411, 1999.

Abrahams, J.M. et al., "Topic Review: Surface Modifications Enhancing Biological Activity of Guglielmi Detachable Coils in Treating Intracranial Aneurysms", Surg. Neurol. 54:34-41, 2000.

FORMING A CHEMICALLY CROSS-LINKED PARTICLE OF A DESIRED SHAPE AND DIAMETER

CROSS-REFERENCE TO RELATED APPLICATIONS

This application is a continuation application of, and claims priority under 35 U.S.C. § 120 to, U.S. application Ser. No. 11/394,691, filed on Mar. 31, 2006, now U.S. Pat. No. 7,288,319 which is a continuation of Ser. No. 10/402,068, now U.S. Pat. No. 7,053,134, filed on Mar. 28, 2003, which is a continuation of U.S. application Ser. No. 10/116,330, filed on Apr. 4, 2002, now abandoned each of which is incorporated herein by reference in its entirety.

TECHNICAL FIELD

The invention relates generally to forming a chemically cross-linked particle and more particularly to forming a chemically cross-linked particle of a desired shape and diameter.

BACKGROUND INFORMATION

Polymeric microspheres (i.e., microspheres formed at least in part from a polymer) are used in medical and industrial areas. These microspheres may be used as drug delivery agents, tissue bulking agents, tissue engineering agents, and embolization agents, for example. Accordingly, there are a variety of methods directed towards preparing polymeric microspheres. Typical methods include dispersion polymerization of the monomer, potentiometric dispersion of dissolved polymer within an emulsifying solution followed by solvent evaporation, electrostatically controlled extrusion, and injection of dissolved polymer into an emulsifying solution through a porous membrane followed by solvent evaporation.

Additional methods of preparing polymeric microspheres include vibratory excitation of a laminar jet of monomeric material flowing in a continuous liquid medium containing a suitable suspending agent, irradiation of slowly thawing frozen monomer drops, emulsification and evaporation, emulsification and evaporation using a high shear air flow, and continuous injection of dissolved polymer into a flowing non-solvent through a needle oriented in parallel to the direction of flow of the non-solvent.

SUMMARY OF THE INVENTION

The present invention facilitates production of microspheres having small diameters in a manner that is generally independent of viscosity and density. This is accomplished through the use of an uncross-linked polymer precursor in solid form, and a mechanical technique of compacting the precursor into a desired shape.

Accordingly, in one aspect, the invention involves a method of forming a chemically cross-linked particle of a desired shape and diameter. The method includes providing an uncross-linked resin (e.g., polyvinyl alcohol) in particulate form, agglomerating the resin into a mass of a desired shape with a desired diameter, compressing the mass, and cross-linking the mass to thereby form the chemically cross-linked particle. An advantage of the present invention is the ability to avoid melting the resin in order to attain the desired shape. This is useful, for example, in connection with thermally unstable polymers.

In one embodiment, the method further includes adding a binding agent (such as a starch or a sugar) to the resin and later removing the binding agent by exposing the particle to a solvent formulated to selectively dissolve the binding agent. The binding agent serves to hold the mass of uncross-linked resin particles together in the desired shape until the mass is cross-linked. In other embodiments, the binding agent comprises a polymer having a melting temperature lower than the melting temperature of the resin. In this way, the polymer becomes part of the chemically cross-linked particle.

In another embodiment, the method further includes cross-linking the mass by exposing the mass to actinic energy such as an electron beam, ultraviolet radiation, or gamma radiation.

In still another embodiment, the method further includes cross-linking the mass by exposing the particle to a gaseous cross-linking agent.

In yet another embodiment, the method further includes agglomerating the resin into a mass in the shape of a sphere with a diameter of less than 600 microns.

In another aspect, the invention involves a method of forming a chemically cross-linked particle of a desired shape and diameter. The method includes providing an uncross-linked resin in particulate form, adding a binding agent to the resin, and agglomerating the resin into a mass. The method further includes heating the mass to a temperature that is both above the melting point of the binding agent and below the melting point of the resin, compressing the mass into a desired shape with a desired diameter, and cooling the mass to a temperature below the melting point of the binding agent. The mass is then cross-linked to form the chemically cross-linked particle.

In one embodiment, cross-linking the mass includes exposing the mass to actinic energy, such as an electron beam, ultraviolet radiation, or gamma radiation.

In another embodiment, cross-linking the mass includes exposing the mass to a gaseous cross-linking agent.

In still another embodiment, the method further includes removing the binding agent by heating the chemically cross-linked particle to a temperature above the melting point of the binding agent. The binding agent is thereby melted out of the chemically cross-linked particle.

In yet another embodiment, the method further includes removing the binding agent by exposing the particle to a solvent formulated to selectively dissolve the binding agent.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF THE PREFERRED EMBODIMENTS

Figure 1:
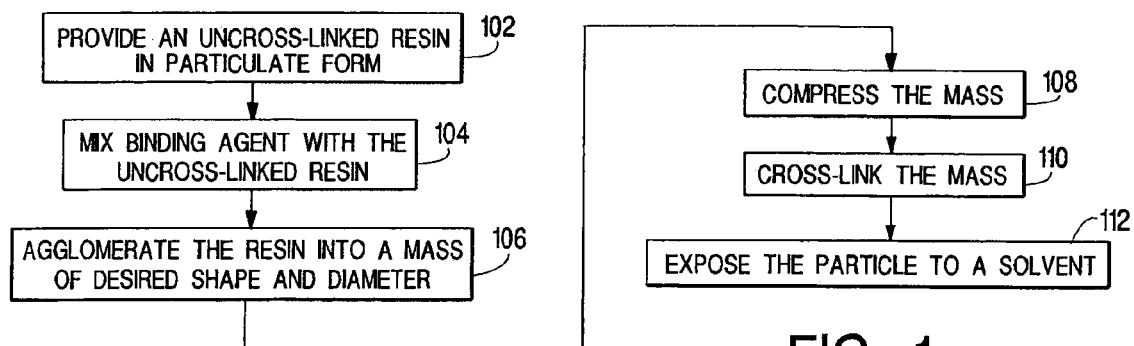
FIG. 1 is an illustrative flow diagram depicting the steps of forming a chemically cross-linked particle of a desired shape and diameter according to one embodiment of the invention.

Referring to FIG. 1, in one embodiment, the method of forming a chemically cross-linked particle of a desired shape and diameter is a mechanical process rather than a chemical process. First, an uncross-linked resin or polymer in particulate form is provided (Step 102). In one embodiment, the resin is a polyvinyl alcohol resin in particulate form having an average diameter of approximately 75 microns, such as a 99% hydrolyzed polyvinyl alcohol (e.g., product #341584 from Aldrich Chemical or Gohsenol NM-11 from Nippon Synthetic Chemical Industry Co.). In other embodiments, polymers such as polyvinyl acetate, vinyl polymers, polyamides, polyureas, polyurethranes, methacrylates, polyvinyl alcohols, or polymers having a pendant ester group that is easily cross-linked (or derivatives thereof) can be used. For many applications (e.g., embolics), the polymer is desirably hydrophilic.

A binding agent is then mixed with the resin particles (Step 104). The binding agent serves to hold the resin particles together before they are cross-linked. In some embodiments, the binding agent is a starch or a sugar (e.g., sucrose). In other embodiments, other materials such as alginates, polysaccharides, proteins, carrageenan, or vegetable gums, for example, can be used as binding agents. In still other embodiments, the binding agent can be a blend of one or more of the above synthetic or naturally occurring materials.

After the uncross-linked resin is mixed with the binding agent, the resin particles are agglomerated into a mass of a desired shape with a desired diameter (Step 106). In one embodiment, the resin particles are forced into a mold (using conventional plastic injection molding techniques) conforming to the desired shape and diameter. In another embodiment, the resin particles are pressed into the desired shape and diameter using conventional compression equipment. In still another embodiment, a punch is used to punch the desired shape out of a solid sheet of the resin. In yet another embodiment, a combination of static electricity and mechanical vibration or agitation is applied to the uncross-linked resin to cause the uncross-linked resin to agglomerate. In another embodiment, the uncross-linked resin particles are agglomerated by being put into a suspension and rotated. Rotation forces the resin particles to collide with each other and form a mass that can thereafter be cross-linked. The size of the mass is selected by controlling the rate of rotation. As the rotation speed increases, so does the number of resin particle collisions. However, the forces acting to pull the agglomerated mass apart also increase. The final size of the mass is a function of rotation speed and the force acting to pull the mass apart.

Preferably, the technique used to form the particle involves, or is followed by, some form of compression in order to ensure that the resin particles stay together in the desired shape, such as a sphere (Step 108). For example, molding can involve pneumatic, hydraulic, or other compression of the resin-filled mold form. Rotation generally provides adequate compression force.

After the mass is compressed, it is cross-linked to form the chemically cross-linked particle (Step 110). In some embodiments, cross-linking the mass is accomplished by exposing the mass to actinic energy, such as an electron beam, ultraviolet radiation, or gamma radiation. In other embodiments, cross-linking the mass is accomplished by exposing the mass to a gaseous cross-linking agent such as formaldehyde, glutaraldehyde, or an acid, for example. Polyvinyl alcohol and other polymers can be cross-linked using any of these techniques.

After the mass is chemically cross-linked and a chemically cross-linked particle is formed, the binding agent may be removed from the particle by exposing the particle to a solvent (Step 112) formulated to selectively dissolve the binding agent. For example, a polar solvent (e.g., water or alcohol) can be used to dissolve the binding agents discussed above.

Figure 2:
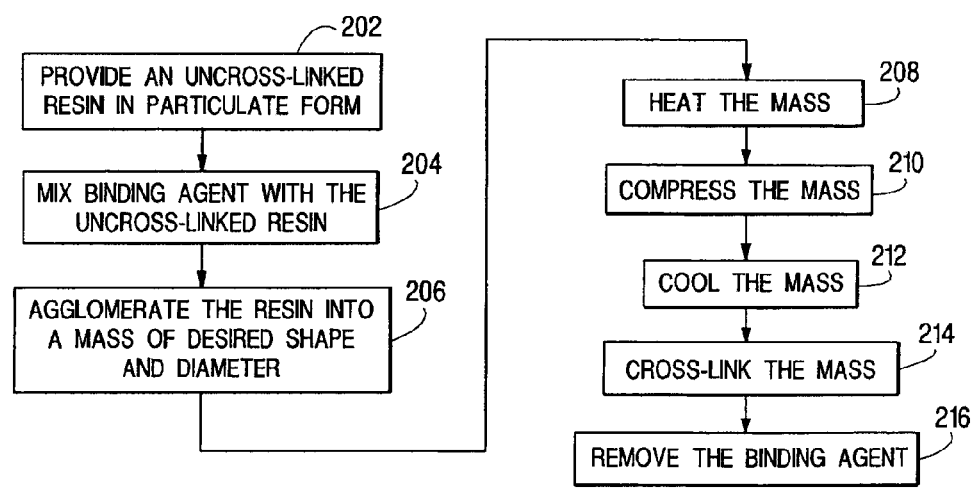
FIG. 2 is an illustrative flow diagram depicting the steps of forming a chemically cross-linked particle of a desired shape and diameter according to another embodiment of the invention.

Referring to FIG. 2, in another embodiment, the binding agent is a polymer with a melting temperature that is lower than the melting temperature of the resin. First, an uncross-linked resin or polymer in particulate form is provided (Step 202). Next, a binding agent is added to the resin (204). After the uncross-linked resin is mixed with the binding agent, the resin particles are agglomerated into a mass of a desired shape with a desired diameter (Step 206).

Exemplary binding agents useful in connection with this embodiment include Methocell methoylcellulose, hydroxypropyl methylcellulose, Ethocell Standard and Premium (organic solvent soluble) from Dow Chemical Co., Avicel PH-001 and Avicell PH-002 microcrystalline cellulose (water soluble) from Asahi Kasei Corp, potassium alginates, sodium alginates, or PEG 1400 (polyethylene glycol), for example. The agglomerated mass of binding agent and resin is heated to a temperature above the binding-agent melting point but below the resin melting point (Step 208). After the mass is heated, it is compressed (Step 210). Compression ensures that the resin particles stay together in the desired shape, such as a sphere, for example. After the mass is compressed, it is cooled (Step 212). Upon cooling, the binding agent resolidifies and the shape imparted to the mass remains "set."

After the mass is cooled, it is then cross-linked to form the chemically cross-linked particle (Step 214). The binding agent may remain in the particle during and following cross-linking of the resin. In some embodiments, cross-linking the mass is accomplished by exposing the mass to actinic energy, such as an electron beam, ultraviolet radiation, or gamma radiation. hi other embodiments, cross-linking the mass is accomplished by exposing the mass to a gaseous cross-linking agent such as formaldehyde or glutaraldehyde, for example. After the mass is cross-linked, the resulting particle can be again heated to a temperature above the binding-agent melting point so that the binding agent can be melted out of the particle (Step 216). The binding agent may also be removed from the particle by exposing the particle to a solvent formulated to selectively dissolve the binding agent. For example, a polar solvent (e.g. water or alcohol) can be used to dissolve some of binding agents discussed above.

Variations, modifications, and other implementations of what is described herein may occur to those of ordinary skill in the art without departing from the spirit and scope of the invention. Accordingly, the invention is not to be defined only by the preceding illustrative description.

What is claimed is:

1. A method comprising:
   providing an uncross-linked polyvinyl alcohol resin;
   agglomerating the polyvinyl alcohol resin into a mass; and
   cross-linking the mass to thereby form a cross-linked particle.

2. The method of claim 1 further comprising adding a binding agent to the polyvinyl alcohol resin.

3. The method of claim 2 wherein adding a binding agent comprises adding a starch.

4. The method of claim 2 wherein adding a binding agent comprises adding a sugar.

5. The method of claim 1 wherein cross-linking the mass comprises exposing the mass to actinic energy.

6. The method of claim 5 wherein exposing the mass to actinic energy comprises exposing the mass to one of an electron beam, ultraviolet radiation, and gamma radiation.

7. The method of claim 1 wherein cross-linking the mass comprises exposing the mass to a gaseous cross-linking agent.

8. The method of claim 2 further comprising removing the binding agent by exposing the particle to a solvent formulated to selectively dissolve the binding agent.

9. The method of claim 1 wherein agglomerating the polyvinyl alcohol resin into a mass comprises agglomerating the polyvinyl alcohol resin into a mass in the shape of a sphere with a diameter of less than 600 microns.

10. A method comprising:
providing an uncross-linked polyvinyl alcohol resin;
adding a binding agent to the polyvinyl alcohol resin, the binding agent having a melting point below a melting point of the polyvinyl alcohol resin;
agglomerating the polyvinyl alcohol resin into a mass;
heating the mass to a temperature above the melting point of the binding agent and below the melting point of the polyvinyl alcohol resin;
cooling the mass to a temperature below the melting point of the binding agent; and
cross-linking the mass to thereby form a cross-linked particle.

11. The method of claim 10 wherein the binding agent is a polymer, the polymer becoming part of the cross-linked particle.

12. The method of claim 10 wherein cross-linking the mass comprises exposing the mass to actinic energy.

13. The method of claim 12 wherein exposing the mass to actinic energy comprises exposing the mass to one of an electron beam, ultraviolet radiation, and gamma radiation.

14. The method of claim 10 wherein cross-linking the mass comprises exposing the mass to a gaseous cross-linking agent.

15. The method of claim 10 further comprising removing the binding agent by heating the chemically cross-linked particle to a temperature above the melting point of the binding agent thereby melting the binding agent out of the cross-linked particle.

16. The method of claim 10 further comprising removing the binding agent by exposing the particle to a solvent formulated to selectively dissolve the binding agent.

17. The method of claim 2, wherein the binding agent is selected from the group consisting of alginates, polysaccharides, proteins, carrageenan, vegetable gums, methylcellulose, hydroxypropyl methylcellulose, and polyethylene glycol.

18. The method of claim 2, wherein the binding agent is selected from the group consisting of potassium alginates and sodium alginates.

19. The method of claim 10, wherein the binding agent is selected from the group consisting of alginates, polysaccharides, proteins, carrageenan, vegetable gums, methylcellulose, hydroxypropyl methylcellulose, and polyethylene glycol.

20. The method of claim 10, wherein the binding agent is selected from the group consisting of potassium alginates and sodium alginates.

21. The method of claim 10, wherein agglomerating the polyvinyl alcohol resin into a mass comprises agglomerating the polyvinyl alcohol resin into a mass in the shape of a sphere with a diameter of less than 600 microns.

* * * * *